United States Patent [19]

Devchand et al.

[11] Patent Number: 5,171,672
[45] Date of Patent: Dec. 15, 1992

[54] RECOMBINANT DNA SYSTEM FOR ASPERGILLUS

[75] Inventors: Medhavinee Devchand, Oakville; David I. Gwynne, Beverly, both of Canada

[73] Assignee: Allelix Biopharmaceuticals Inc., Ontario, Canada

[21] Appl. No.: 401,319

[22] Filed: Aug. 31, 1989

[51] Int. Cl.$^5$ .................. C12N 15/80; C12N 15/11; C12N 1/15

[52] U.S. Cl. .................. 435/69.1; 435/254; 536/27

[58] Field of Search .................. 536/27; 435/69.1, 435/71.1, 91, 171, 172.1, 172.3, 254, 320.1, 913; 935/6, 8, 9, 22, 24, 33, 34, 36, 47, 48, 59, 60, 61, 66, 68

[56] References Cited

PUBLICATIONS

Gwynne et al., Gene 51:205-216 (1987).
Gwynne et al., 1987, Bio./Technology, 5:713-719.
Pickett et al., 1987, Gene 51:217-226.
Warburton et al., 1983, NAR, 11/17:5837-5854.
Sealy-Lewis et al., "Regulation of two alcohol . . . " Current Genetics, 1984, :8:253 Lockington et al. Cloning & Characterization . . . Gene, 1985, 33:137.
Lockington et al. "Regulation of alcR . . . " Molecular Microbiology, 1987, 1(3):275.
Lagosky et al. "Molecular . . . " Nucl. Acids. Res. 1987 15(24): 10355.
Feienbok et al. "The ethanol regulon . . . " Gene, 1988, 73:385.

*Primary Examiner*—Richard A. Schwartz
*Assistant Examiner*—Nancy T. Vogel
*Attorney, Agent, or Firm*—Nixon & Vanderhye

[57] ABSTRACT

The invention relates to constitutive promoters useful to control gene expression in Aspergillus hosts. The promoters are derived from the *Aspergillus nidulans* aldA gene.

5 Claims, 4 Drawing Sheets

```
        ATCGCGAGCTCTTCAACGTGTTTTCAGAATCATCTAGGCTCGTGGAGGCA
  -350----------------------------------------------+
        TAGCGGTCGACAAGTTGCACAAAAGTCTTAGTAGATCCGAGCACCTCCGT

GTGGGCACCGCGGCGAAGGGGACGGAATGCAGTTCACCTGGACTGGCTCT
  -300----------------------------------------------+
        CACCCGTGGCGCCGCTTCCCCTGCCTTACGTCAAGTGGACCTGACCGAGA
10

TGAAGACCAGTGGGGCACTTCGGCGGGTTGCTAGCTTGCTACATGTAATT
  -250----------------------------------------------+
        ACTTCTGGTCACCCCGTGAAGCCGCCCAACGATCGAACGATGTACATTAA
15

TCCATGGGTAACAGCTATCCTCAACAAGAGCGGCTCCGCTTGACCTGTTC
  -200----------------------------------------------+
        AGGTACCCATTGTCGATAGGAGTTGTTCTCGCCGAGGCGAACTGGACAAG
20

CCCTCCTTTCCCCTCTTTTGCTGCGACCACTGGCTCAGTGCTACCAAAGC
  -150----------------------------------------··········+
        GGGAGGAAAGGGGAGAAAACGACGCTGGTGACCGAGTCACGATGGCCCCG
25

CAGAGCGGTATTATTAAGCTCCCTCGTCCTCCCACCGAGCCAGCATTTC
  -100·············································+
        GTCTCGCCATAATAATTTCGAGGGAGCAGGAGGGTGGCTCGGTCGTAAAG

TCCCTACTCCAACTCTCCTCTCCCAAGATACCCATATTTCCCGCTCACCATG
  -50··········································Met
        AGGGATGAGGTTGAGAGGAGAGGGTTCTATGGGTATAAAGGGCGAGTGGTAC
```

FIG. 1

```
         ATCGCGAGCTCTTCAACGTGTTTTCAGAATCATCTAGGCTCGTGGAGGCA
    -350─────────────────────────────────────────────────+
         TAGCGGTCGACAAGTTGCACAAAAGTCTTAGTAGATCCGAGCACCTCCGT

GTGGGCACCGCGGCGAAGGGGACGGAATGCAGTTCACCTGGACTGGCTCT
    -300─────────────────────────────────────────────────+
         CACCCGTGGCGCCGCTTCCCCTGCCTTACGTCAAGTGGACCTGACCGAGA

TGAAGACCAGTGGGGCACTTCGGCGGGTTGCTAGCTTGCTACATGTAATT
    -250─────────────────────────────────────────────────+
         ACTTCTGGTCACCCCGTGAAGCCGCCCAACGATCGAACGATGTACATTAA

TCCATGGGTAACAGCTATCCTCAACAAGAGCGGCTCCGCTTGACCTGTTC
    -200─────────────────────────────────────────────────+
         AGGTACCCATTGTCGATAGGAGTTGTTCTCGCCGAGGCGAACTGGACAAG

CCCTCCTTTCCCCTCTTTTGCTGCGACCACTGGCTCAGTGCTACCAAAGC
    -150──────────────────────────────────────**************+
         GGGAGGAAAGGGGAGAAAACGACGCTGGTGACCGAGTCACGATGGCCCCG

CAGAGCGGTATTATTAAGCTCCCTCGTCCTCCCACCGAGCCAGCATTTC
    -100**************************************************+
         GTCTCGCCATAATAATTTCGAGGGAGCAGGAGGGTGGCTCGGTCGTAAAG

TCCCTACTCCAACTCTCCTCTCCCAAGATACCCATATTTCCCGCTCACCATG
    -50-***********************************************Met
         AGGGATGAGGTTGAGAGGAGAGGGTTCTATGGGTATAAAGGGCGAGTGGTAC
```

RECOMBINANT DNA SYSTEM FOR ASPERGILLUS

This invention relates to the production of heterologous proteins in Aspergillus hosts. More particularly, the invention relates to recombinant DNA expression constructs which incorporate a promoter derived from the aldehyde dehydrogenase gene of *Aspergillus nidulans* and to use of those constructs in developing Aspergillus strains that produce heterologous proteins.

In *Aspergillus nidulans*, expression of both the aldehyde dehydrogenase gene (aldA) and its companion alcohol dehydrogenase gene (alcA) is controlled by the same tightly regulated system of induction and repression. That is, expression of both genes is repressed by a carbon catabolite mechanism mediated by the creA gene product and high glucose concentrations. Expression of both genes is further controlled by an induction mechanism mediated by a combination of the alcR gene product and an inducer such as threonine. Thus, expression of these genes occurs only when *A. nidulans* is grown under glucose-depleted, inducer-rich conditions.

The 5'-untranslated region i.e. the promoter region, of these and other regulated Aspergillus genes have been exploited recently to drive the production of heterologous proteins in genetically engineered Aspergillus hosts. To accomplish this, recombinant DNA expression constructs have been prepared in which DNA coding for the heterologous protein is placed under expression control of a promoter region excised from a regulated Aspergillus gene. The construct is then introduced into a selected Aspergillus host, usually by plasmid-mediated transformation. Production of the heterologous protein is then achieved by culturing the transformed Aspergillus strain under inducing conditions necessary for proper functioning of the promoter contained on the expression cassette. When cassettes based on the alcA or aldA promoter regions are used, for example, strains must be cultured in the presence of threonine or a functionally equivalent inducer agent in order for protein production to occur (see Gwynne et al, Bio/Technology, July 1987, 713-719).

Though good yields of heterologous proteins have been obtained from Aspergillus strains using regulated promoters, the use of such promoters can be complicated by their dependence on inducing agents. In addition to the cost and inconvenience of adding inducer to the medium in which the production strain is cultured, specialized equipment can be required to control the rate at which the inducer is added during fermentation.

It is an object of the present invention to provide promoters useful to achieve constitutive expression i.e. inducer-independent expression, of heterologous proteins in Aspergillus hosts.

SUMMARY OF THE INVENTION

It has now been found that the tightly regulated aldehyde dehydrogenase gene (aldA) of *Aspergillus nidulans* can be tapped to provide promoters that function in a non-regulated manner. More particularly, it has been found that DNA sequences located within the promoter region of the aldA gene exhibit constitutive promoter activity when upstream regulatory elements specifying glucose repression and inducer-dependence are absent.

According to one aspect of the invention, there is provided a DNA molecule that has a nucleotide sequence which corresponds to a region of the *Aspergillus nidulans* aldA gene which exhibits constitutive promoter activity.

According to another aspect of the invention, there is provided a recombinant DNA expression construct useful in developing Aspergillus strains that produce heterologous protein in a constitutive manner. The recombinant DNA expression constructs of the invention comprise protein-encoding DNA linked operably to a constitutive promoter, the nucleotide sequence of which corresponds to a region of the *A. nidulans* aldA gene which exhibits constitutive promoter activity.

According to another aspect of the invention, there is provided an Aspergillus strain which, upon culturing, produces heterologous protein in a constitutive manner as a result of having been transformed by a recombinant DNA expression construct of the invention.

BRIEF REFERENCE TO THE DRAWINGS

FIG. 1 provides the nucleotide sequence of a 5' portion of the aldehyde dehydrogenase gene. Asterisks are used to identify the minimum region thereof which exhibits constitutive promoter activity;

DESCRIPTION OF THE INVENTION AND ITS PREFERRED EMBODIMENTS

Figure 2:
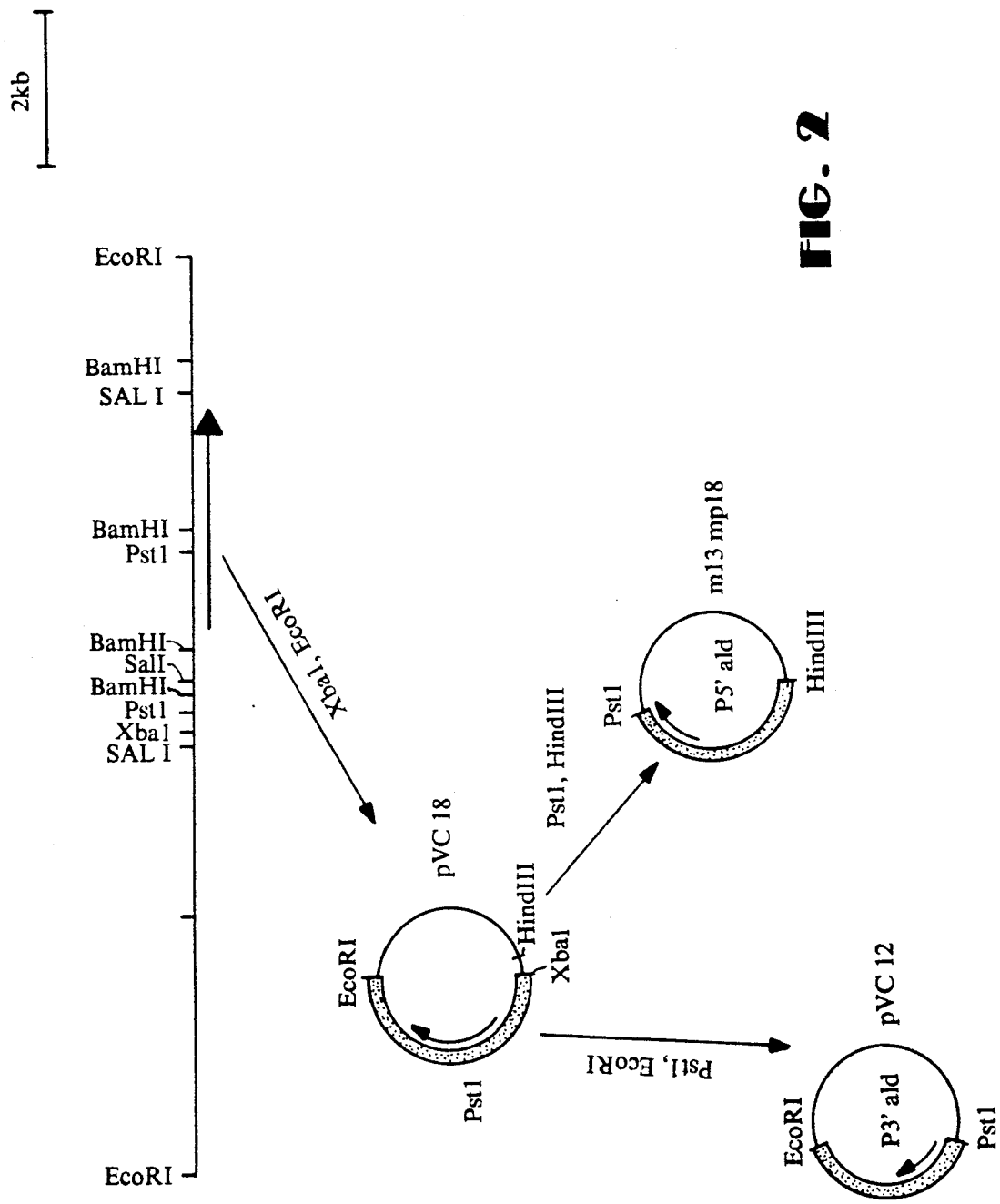
FIG. 2 illustrates schematically the steps taken to clone the aldA gene.

The constitutive promoters of the invention are characterized as DNA molecules having a nucleotide sequence that corresponds to at least the first 110 nucleotides upstream (5') of the aldA initiation codon (ATG). The specific sequence of this preferred constitutive promoter is identified by the use of asterisks in FIG. 1. Segments of the aldA promoter region extending from the initiation codon beyond nucleotide-110 may also be employed as constitutive promoters, if desired, although it should be recognized that inducer-dependency of the promoter may be restored when sequences upstream of nucleotide-130 are incorporated.

The constitutive promoters of the present invention may be obtained using any of a variety of techniques. Restriction sites may be incorporated into the promoter region of a cloned aldA gene, for example, so that DNA sequences exhibiting constitutive promoter activity may be excised. Alternatively, the aldA gene may be resected to remove DNA sequences upstream of the constitutive promoter region and then mutagenized near the initiation codon to provide a restriction site for the release of the constitutive promoter from the remainder of the aldA gene. Further, having herein provided the nucleotide sequence of the constitutive promoters, it will be appreciated that they may be synthesized using techniques, such as the phosphoramidite technique, now standard in the gene synthesis art. As a further option, the constitutive promoters of the invention may be obtained using the polymerase chain reaction technology. In this latter approach, *A. nidulans* genomic DNA or the aldA gene may be incubated with primers specific for the nucleotide ends of the constitutive promoter so that only the constitutive promoter region of the aldA gene is amplified and recovered.

In general, the promoters of the present invention are exploited in substantially the same manner as other promoters developed for use in Aspergillus hosts. That is, recombinant DNA expression constructs based thereon are first prepared by operably linking protein-encoding DNA with the constitutive promoter, such that expression of the protein-encoding DNA is controlled by the constitutive promoter. These constructs are then introduced into Aspergillus hosts by DNA-mediated transformation, using protocols and selectable markers adapted for the particular Aspergillus species chosen as the protein production host. Following transformation, strains harbouring the recombinant DNA constructs as genomic inserts are identified and then cultured in standard Aspergillus growth medium. Significantly, the constitutive promoters of the invention eliminate the need for growth medium supplements such as inducers that are otherwise required when regulated promoters are employed to control expression of desired proteins.

The protein-encoding DNA incorporated on the recombinant DNA constructs of the invention may code for any of a variety of heterologous proteins i.e. proteins foreign to the Aspergillus host. Included among such heterologous proteins are mammalian proteins having therapeutic value such as the interleukins and the growth factors and various serum proteins. Commercially valuable enzymes may also be expressed, such as chymosin and glucoamylase. It should be appreciated, however, that because of the continuous expression of the protein by the constitutive promoter, the present system may not be suitable for intracellular expression of proteins that are toxic to, or significantly inhibit the growth of, the Aspergillus host.

According to a preferred embodiment, the recombinant DNA constructs incorporate DNA coding for a signal peptide that permits the desired protein encoded thereon to be secreted to the medium in which the transformed Aspergillus host is grown. To enable secretion, the signal peptide-encoding DNA is linked operably to the DNA coding for the desired protein, so that expression from the constitutive promoter yields a fusion protein bearing an N-terminal signal peptide. Secretion may be achieved using signal peptides native to proteins of Aspergillus or of heterologous origin.

Once prepared, the recombinant DNA construct may be introduced into a chosen Aspergillus host using strategies established in the art. Typically, the construct is introduced together with a selectable marker using the DNA-mediated transformation approach. Preferably the Aspergillus host is selected from *Aspergillus niger*, *Aspergillus nidulans* and *Aspergillus oryzae*. To transform *Aspergillus niger*, for example, an argB-strain thereof may be transformed using bacterial plasmids that harbour the recombinant DNA construct of the invention and the argB gene, according to the protocol reported by Buxton et al in Gene 37, 1985, 207-214. *Aspergillus oryzae* transformation may be achieved using, for example, the protocol described by Christensen et al in Bio/-Technology, Vol. 6, December 1988, 1419-1422.

EXAMPLE 1

Identification of the constitutive promoter region of the A. nidulans aldA gene

DNA sequences within the aldA gene that exhibit constitutive promoter activity were identified during the course of expression studies designed to locate elements within the promoter region of the aldA gene that mediate its threonine-dependent expression. In these studies, a genomic clone containing the aldA gene, which was isolated from an *A. nidulans* genomic library in Lambda Charon 4A as described by Pickett et al in Gene 51, 1987, was used. A restriction endonuclease map of the genomic clone is provided in FIG. 2. The black arrow appearing on FIG. 2 identifies the location of the aldA gene contained thereon.

To perform deletion analysis of the aldA promoter region, a 6.8 kb EcoRI-XbaI fragment containing the aldA gene was first subcloned into bacterial plasmid pUC18. For convenience, an internal PstI site was utilized to generate a 3' EcoRI-PstI fragment which was subcloned into pUC12 to form p3'ald, and a 5' PstI-HindIII fragment which was subcloned into M13mp18 to generate construct p5'ald, as shown in FIG. 3.

Figure 3:
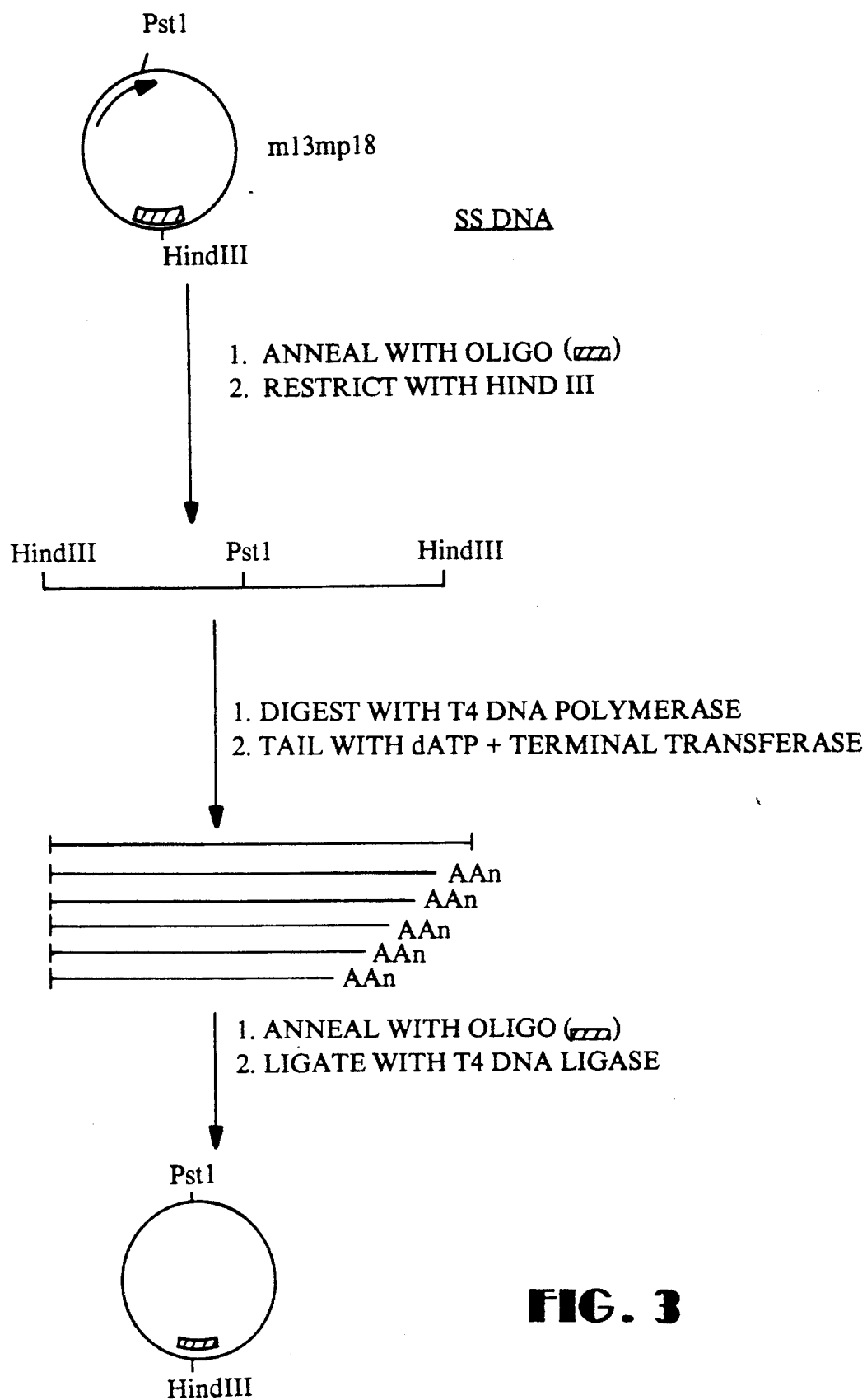
FIG. 3 illustrates schematically the construction of 5' deletion derivatives of the aldA gene.

To generate resection mutants as shown in FIG. 3, single-stranded DNA from p5'ald was linearized by restricting with HindIII. The exonuclease activity of T4 DNA polymerase was then used to digest into the HindIII site towards the PstI site of the fragment. Resection was terminated upstream of the aldA coding region by limiting incubation to no longer than 30 minutes i.e. from about 20 to 30 minutes. The resected fragments were then tailed and recircularized as shown in FIG. 3 and transformed into *E. coli* hosts for amplification and selection. Resecton mutants of appropriate size were then released by restriction with HindIII and PstI and cloned into the p3'ald plasmid, thereby regenerating the full coding region of aldA, preceded by a resected promoter region.

To determine whether these aldA mutants functionally expressed aldehyde dehydrogenase, DNA from these mutants was introduced, together with the pyrG gene of *Neurospora crassa*, into an *Aspergillus nidulans* strain deficient in both aldA and pyrG. Transformants were picked randomly and analyzed by Southern blot to ensure the presence of unrearranged copies of the aldA gene. Transformants containing copies of the resected aldA gene were assayed to analyze the regulation of expression of the resected aldA constructs. This involved growth of a particular transformant in minimal medium under either inducing conditions (0.1% fructose and 100 mM threonine), repressing conditions (1% glucose) or non-repressed, non-induced conditions (1% fructose). Spores of transformants obtained following growth for 3 days on fungal complete medium were then inoculated in 50 mL cultures. Mycelia obtained from cultures grown for 24 hours at 37° C. were then harvested and lyophilized. Protein samples were then extracted and assayed.

The aldehyde dehydrogenase assay was performed using the protocol described by Creaser et al, in Int. J. Biochem., 19, 1987, 1009-1012, and involved addition of an aliquot of the extract to assay buffer containing benzaldehyde as substrate and NAD as reporter. Increases in absorbance of NADH were determined spectrophotometrically at 340 nM as a measure of the aldehyde dehydrogenase activity in the samples.

Studies conducted on each of the various transformants surprisingly revealed a number of mutants capable of producing aldehyde dehydrogenase in the absence of inducer and under conditions normally repressive to aldA expression. The results obtained from one such mutant, designated AldΔ28, are compared with those obtained using a control strain T580 which harbours the intact, wild type aldA gene, in Table 1 below:

TABLE 1

| | Levels of Aldehyde Dehydrogenase ($A_{340nm}$/min/mg protein) | | | | |
| --- | --- | --- | --- | --- | --- |
| | Transformants of AldΔ 28 | | | | |
| Growth Conditions | 1 | 2 | 3 | 4 | $T_{580}$ |
| 1. Glucose repressed (0 + 1% glucose) | 26 | 41 | 68 | 23 | 1 |
| 2. Non-induced; non-repressed (0 + 1% fructose) | 22 | 31 | 76 | 12 | 4 |
| 3. Induced (0 + 0.1% fructose + 100 mM threonine) | 34 | 37 | 71 | 16 | 47 |

0 = fungal minimal medium

Nucleotide sequencing of the AldΔ28 gene revealed that the promoter region thereof contained only 110 nucleotides preceding the initiation codon (FIG. 1). Analysis of other mutants capable of expressing aldA constitutively has subsequently revealed that constitutive promoter activity is limited to a region extending no more than 130 bases upstream of the aldA initiation codon.

EXAMPLE 2

Figure 4:
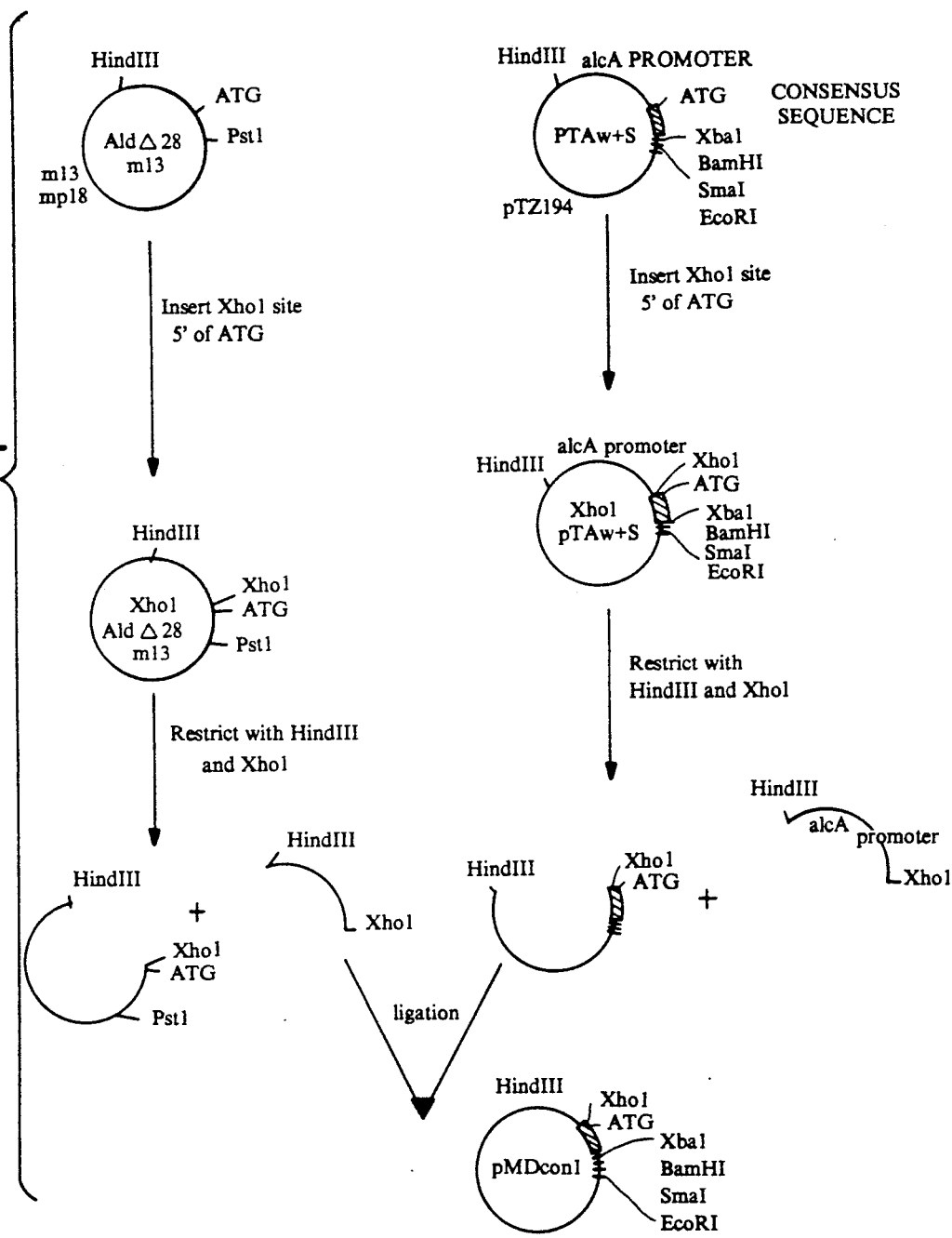
FIG. 4 illustrates the construction of a recombinant DNA expression construct which incorporates the constitutive promoter region of the aldA gene.

Development of recombinant DNA constructs based on the constitutive promoter region of the aldA gene To obtain the 110 bp constitutive promoter contained on resection mutant aldΔ28, a XhoI site was introduced at the initiation codon by oligonucleotide-directed site-specific mutagenesis. This permitted the promoter to be released from AldΔ28 as a HindIII-Xho1 fragment. In the manner illustrated in FIG. 4, the constitutive aldA promoter was then used to replace the regulated alcA promoter contained on Aspergillus secretion vector pTAwtS (see Gwynne et al, Biochemical Society Transactions, Vol. 17, 1989, 338-340). This generated an Aspergillus secretion vector, designated pMDcon1, in which the 110 bp constitutive aldA promoter is linked operably to DNA coding for a signal peptide which bears a 3' multiple cloning site into which DNA coding for proteins of interest may be incorporated.

EXAMPLE 3

Constitutive expression of heterologous protein in *Aspergillus nidulans*

A 1.5 kb EcoR1 fragment of cDNA coding for human corticosteroid binding globulin (CBG) was cloned into the EcoR1 site of pMDcon1, downstream of the signal sequence. Site-specific mutagenesis was then employed to bring the CBG-encoding DNA into direct fusion with the signal sequence. The resulting plasmid, pMDcon1-CBG, was then cotransformed with pFB94 (harbouring the N. crassa pyrG gene) into A. nidulans strain 1448 (aldA deficient, pyrG-). Transformants were then screened by Southern analysis to confirm the presence of genomically integrated pMDcon1-CBG DNA.

Spores of selected transformants were inoculated into 50 mL of minimal medium supplemented with 1% glucose and lacking threonine. After incubation for 48 hours at 30° C. with shaking, both the mycelium and the culture medium were collected. RNA was isolated from the mycelium and subjected to dot blot analysis. The results indicated the presence of CBG-specific mRNA in the transformants harbouring chromosomal copies of the pMDcon1-CBG plasmid. Proteins recovered from spent culture medium were also analyzed by Western blot analysis. A band of ~55 kD was found to have immunoreactivity with anti-human CBG antibody, thus confirming that the aldA constitutive promoter region herein described is capable not only of controlling expression of heterologous proteins in Aspergillus hosts, but of doing so in the absence of inducer normally required for expression from the regulated aldA promoter and in the presence of amounts of glucose that are repressive to the regulated aldA promoter.

We claim:

1. A recombinant DNA expression construct for use in constructing an Aspergillus strain that produces a heterologous protein, said construct comprising DNA coding for said heterologous protein linked operably with a promoter enabling constitutive expression thereof, said constitutive promoter comprising the nucleic acid sequence indicated by asterisks in FIG. 1.

2. The construct according to claim 1, wherein said DNA coding for heterologous protein comprises DNA coding for a signal peptide.

3. An Aspergillus strain which produces a heterologous protein as a result of having been transformed by a recombinant DNA expression construct as defined in claim 1.

4. An Aspergillus strain according to claim 3 wherein said strain is an *Aspergillus nidulans* strain.

5. A method for producing a protein which is heterologous to Aspergillus, which method comprises the step of culturing an Aspergillus strain as defined in claim 4.

* * * * *